United States Patent
Vacanti et al.

[11] Patent Number: 6,123,727
[45] Date of Patent: Sep. 26, 2000

[54] TISSUE ENGINEERED TENDONS AND LIGAMENTS

[75] Inventors: Charles A. Vacanti, Lexington; Yi Lin Cao, Shrewsbury; Robert S. Langer, Newton; Joseph P. Vacanti, Winchester; Keith Paige; Joseph Upton, both of Brookline, all of Mass.

[73] Assignees: Massachusetts Institute of Technology; Cambridge Childern's Medical Center Corproration, Boston, both of Mass.

[21] Appl. No.: 08/905,491

[22] Filed: Aug. 4, 1997

Related U.S. Application Data

[63] Continuation of application No. 08/431,780, May 1, 1995, abandoned.

[51] Int. Cl.[7] ........................................... A61F 2/08
[52] U.S. Cl. ................................................ 623/13
[58] Field of Search .................................. 623/1, 11, 12, 623/13, 15, 16, 66

[56] References Cited

U.S. PATENT DOCUMENTS

| | | | |
|---|---|---|---|
| 4,576,608 | 3/1986 | Homsy | 623/13 |
| 5,019,087 | 5/1991 | Nichols | 623/13 |
| 5,078,744 | 1/1992 | Chvapil | 623/13 |
| 5,092,887 | 3/1992 | Gendler | 623/13 |
| 5,171,273 | 12/1992 | Silver | 623/13 |
| 5,263,984 | 11/1993 | Li et al. | 623/13 |
| 5,376,118 | 12/1994 | Kaplan et al. | 623/13 |

*Primary Examiner*—David J. Isabella
*Attorney, Agent, or Firm*—Clark & Elbing LLP

[57] ABSTRACT

Connective tissue, including neo-tendons and ligaments, has been constructed using biodegradable synthetic scaffolds seeded with tenocytes. The scaffolds are preferably formed from biodegradable fibers formed of a polymer such as polyglycolic acid-polylactic acid copolymers, and seeded with cells isolated from autologous tendon or ligament by means of enzymatic digestion or direct seeding into tissue culture dishes from explants. The cell polymer constructs are then surgically transplanted to replace missing segments of functioning tendon or ligament.

6 Claims, No Drawings

6,123,727

TISSUE ENGINEERED TENDONS AND LIGAMENTS

This is a continuation of application Ser. No. 08/431,780 filed on May 1, 1995 now abandoned.

BACKGROUND OF THE INVENTION

The present invention is generally in the area of forming new tissues by implantation of appropriate cells on a polymer matrix, and is specifically directed towards construction of new tendons and ligaments.

Tissues connecting bones and muscles are collectively referred to herein as "connective tissue". Tendons are tissues which attach muscles to bones; aponeuroses are sheet-like tendons connecting one muscle with another or with bones; ligaments hold bones together at joints. Tendons and ligaments are elongated, cylindric structures formed of dense connective tissue, adapted for tension in one direction, with fibers having an orderly, parallel arrangement. The most common variety of dense regularly arranged connective tissue has a predominance of collagenous (white) fibers arranged in bundles. Fibroblasts are placed in rows between the bundles. The tissue is silvery white, tough, yet somewhat pliable. The collagen bundles of the tendons aggregate into larger bundles that are enveloped by loose connective tissue containing blood vessels and nerves. Externally, the tendon is surrounded by a sheath of dense connective tissue.

An essential characteristic of connective tissue is its strength and ability to stretch or be pulled, then regain its original shape. When damaged, the orderly structure which imparts this ability to the connective tissue is disrupted and usually does not heal to yield a fully functional tissue.

Tendon defects, regardless of their origin, often prove to be difficult problems for orthopedic surgery and hand surgery. An ideal reconstruction repairs the defect with an autologous tendon graft. Autogenous tendon usage is limited by availability and donor site morbidity. Consequently, other approaches have been used: homo- or heterografts and artificial tendons. Homo- or heterografts, though, suffer from a scarcity of supply, increased susceptibility to infection, and concerns about possible transmission of infectious agents.

A carbon fiber implant for reconstructing severely torn ligaments and tendons has been developed which consists of carbon fibers coated with a polymer such as polylactic acid, as discussed in "Principles of Human Anatomy" by G. J. Tortora, 5th edition (Harper & Row, New York 1989). The coated fibers are sewn in and around torn ligaments and tendons to reinforce them and to provide a scaffolding around which the body's own collagenous fibers grow. The polymer is hydrolysed within the body over time and the carbon fibers eventually fracture, typically within two weeks. During this time, fibroblasts coat the fibers with collagen. The original structure of the tendons is not maintained, however, and the repaired tendon lacks strength and flexibility. Artificial prostheses, although not infectious, are also susceptible to infection, extrusion, and uncertain long-term immunologic interactions with the host. Moreover, prostheses cannot adapt to environmental stresses as do living tendon tissue and have a high incidence of adhesive breakdown at their interface with the host.

It is therefore an object of the present invention to provide a method and materials for creating new tendons and ligaments which have the strength and flexibility of normal tendons and ligaments.

It is a further object of the present invention to provide a method and materials for creating new tendons and ligaments which leaves no foreign materials in the body nor elicits an immunological reaction against the new tendons or ligaments.

SUMMARY OF THE INVENTION

Connective tissue, including neo-tendons and ligaments, has been constructed using biodegradable synthetic scaffolds seeded with tenocytes. The scaffolds are preferably formed from biodegradable fibers formed of a polymer such as polyglycolic acid-polylactic acid copolymers, and seeded with cells isolated from autologous tendon or ligament by means of enzymatic digestion or direct seeding into tissue culture dishes from explants. The cell polymer constructs are then surgically transplanted to replace missing segments of functioning tendon or ligament.

As shown by the examples, transplanted tenocytes attached to biodegradable synthetic polymer scaffolds to generate new tendon in mice. Tenocytes were isolated from freshly slaughtered newborn calf tendon and were seeded onto a non-woven mesh of polyglycolic acid, arranged as either a random array of fibers, or as fibers in parallel. The cell-polymer constructs were implanted into the mice subcutaneously. Specimens were harvested after six to ten weeks and examined. On gross examination, all specimens closely resembled tendons from which the cells had initially been isolated. Histologic evaluation demonstrated that collagen bundles appeared to be organizing in a parallel fashion at the lateral aspects and appeared very similar to the collagen bundles seen in normal tendon. Centrally, the collagen fibrils appeared to be randomly oriented. Specimens that were created from implantation of parallel polymer fibers appeared to have a greater degree of parallel collagen fibril orientation at an earlier time period. The neo-tendon constructs demonstrated moderate tensile strength when stretched.

DETAILED DESCRIPTION OF THE INVENTION

A method and materials to form connective tissue, especially tendons and ligaments, is described wherein cells obtained from tendons (tenocytes) or ligaments (ligamentum cells) are seeded onto and into biodegradable, biocompatible synthetic polymeric fibers, then implanted to form the desired connective tissue.

Cells for Implantation

A variety of cells can be used to form connective tissue. Tenocytes and ligamentum cells are the preferred cells. Fibroblasts differentiate to form collagen and can also be used. Dermal fibroblasts are preferred. Chondrocytes form collagen and can therefore be used, but are not as preferred.

Autologous cells obtained by a biopsy are most preferred. Cells are isolated from autologous tendon or ligament by excision of tissue, then either enzymatic digestion of cells to yield dissociated cells or mincing of tissue to form explants which are grown in cell culture to yield cells for seeding onto matrices. To obtain cells, the area to be biopsied can be locally anesthetized with a small amount of lidocaine injected subcutaneously. Alternatively, a small patch of lidocaine jelly can be applied over the area to be biopsied and left in place for a period of 5 to 20 minutes, prior to obtaining biopsy specimen. The biopsy can be obtained with the use of a biopsy needle, a rapid action needle which makes the procedure extremely simple and almost painless. This small biopsy core of tissue can then be transferred to media consisting of phosphate buffered saline, divided into very small pieces which are adhered to a culture plate, and serum containing media added. Cells are dissociated as described below in the examples using standard techniques, such as treatment with collagenase or trypsin. Alternatively, the tissue biopsy can be minced and the cells dispersed in a culture plate with any of the routinely used medias. After cell expansion within the culture plate, the cells can be passaged utilizing the usual technique until an adequate number of cells is achieved.

They can be maintained and/or proliferated in culture until implanted, either in standard cell culture dishes or after seeding onto matrices, as described below. Alternatively, cells can be seeded into and onto the matrix at the time of implantation.

Polymeric Matrices

Matrix Configuration

For a tendon or ligament to be constructed, successfully implanted, and function, the matrices must have sufficient surface area and exposure to nutrients such that cellular growth and differentiation can occur following implantation. The organization of the tissue may be regulated by the microstructure of the matrix. Specific pore sizes and structures may be utilized to control the pattern and extent of fibrovascular tissue ingrowth from the host, as well as the organization of the implanted cells. The surface geometry and chemistry of the matrix may be regulated to control the adhesion, organization, and function of implanted cells or host cells.

In the preferred embodiment, the matrix is formed of polymers having a fibrous structure which has sufficient interstitial spacing to allow for free diffusion of nutrients and gases to cells attached to the matrix surface until vascularization and engraftment of new tissue occurs. During this period of time, the implanted cells secrete new matrix which includes a parallel arrangement of type 1 collagen fibers as the polymer support scaffolding degrades. The interstitial spacing is typically in the range of 50 to 300 microns. As used herein, "fibrous" includes one or more fibers that is entwined with itself, multiple fibers in a woven or non-woven mesh, and sponge like devices.

Polymers

The matrices are formed of synthetic, biodegradable, biocompatible polymers. The term "bioerodible", or "biodegradable", as used herein refers to materials which are enzymatically or chemically degraded in vivo into simpler chemical species. "Biocompatible" refers to materials which do not elicit a strong immunological reaction against the material nor are toxic, and which degrade into non-toxic, non-immunogenic chemical species which are removed from the body by excretion or metabolism.

In addition to biocompatibility, key characteristics of the polymer are that it must be processable into fibers of an appropriate length, thickness, and strength for use as a matrix that serves to form new tendons or ligaments and it must degrade within the desired time frame, preferably six to twelve weeks, but optionally up to a few months or even a year.

Fibers can be formed by melt-spinning, extrusion, casting, or other techniques well known in the polymer processing area. Preferred solvents, if used, are those which are completely removed by the processing or which are biocompatible in the amounts remaining after processing.

Examples of polymers which can be used include natural and synthetic polymers, although synthetic polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyamino acids, polyortho esters, polyacetals, degradable polycyanoacrylates and degradable polyurethanes. Examples of natural polymers include proteins such as albumin, collagen, fibrin, and synthetic polyamino acids, and polysaccharides such as alginate, heparin, and other naturally occurring biodegradable polymers of sugar units.

PLA, PGA and PLA/PGA copolymers are particularly useful for forming the biodegradable matrices. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. Nos. 1,995,970 to Dorough; 2,703,316 to Schneider; 2,758,987 to Salzberg; 2,951,828 to Zeile; 2,676,945 to Higgins; and 2,683,136; 3,531,561 to Trehu.

PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", *Chemistry and Industry*, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. A preferred material is poly(lactide-co-glycolide) (50:50), which degrades in about six weeks following implantation (between one and two months).

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

Polymer Coatings

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture. A preferred material for coating the polymeric matrix is polyvinyl alcohol or collagen.

Additives to Polymer Matrices

In some embodiments it may be desirable to add bioactive molecules to the cells. A variety of bioactive molecules can be delivered using the matrices described herein. These are referred to generically herein as "factors" or "bioactive factors".

In the preferred embodiment, the bioactive factors are growth factors. Examples of growth factors include heparin binding growth factor (hbgf), transforming growth factor alpha or beta (TGFβ), alpha fibroblastic growth factor (FGF), epidermal growth factor (TGF), vascular endothelium growth factor (VEGF), some of which are also angiogenic factors. In some embodiments it may be desirable to incorporate factors such as nerve growth factor (NGF) or muscle morphogenic factor (MMP). Steroidal antiinflammatories can be used to decrease inflammation to the implanted matrix, thereby decreasing the amount of fibroblast tissue growing into the matrix.

These factors are known to those skilled in the art and are available commercially or described in the literature. In vivo dosages are calculated based on in vitro release studies in cell culture; an effective dosage is that dosage which increases cell proliferation or survival as compared with controls, as described in more detail in the following examples. Preferably, the bioactive factors are incorporated to between one and 30% by weight, although the factors can be incorporated to a weight percentage between 0.01 and 30% weight percentage.

Bioactive molecules can be incorporated into the matrix and released over time by diffusion and/or degradation of the matrix, or they can be suspended with the cell suspension.

Implantation

The matrices are implanted in the same manner as other reconstructed or prosthetic tendons or ligaments. They are surgically interposed between the cut ends of autologous tendon and sutured in place with biodegradable suture material.

The tendons and ligaments and other connective tissue are useful for repair and reconstruction of congenital defects as well as traumatic defects. The neo-connective tissue is therefore useful in plastic surgery for cosmetic purposes as well as in reconstructive surgery.

The present invention will be further understood by reference to the following non-limiting examples evaluating the feasibility of transplanted tenocytes attached to biodegradable synthetic polymer scaffolds to generate new tendon in athymic mice. Tenocytes were isolated from freshly slaughtered newborn calf tendon and were seeded onto a non-woven mesh of polyglycolic acid, arranged as either a random array of fibers, or as fibers in parallel. The cell-polymer constructs were implanted into athymic mice subcutaneously. Specimens were harvested after 6–10 weeks and examined. On gross examination, all specimens (n=25) closely resembled tendons from which the cells had initially been isolated after 6 weeks on in vivo incubation. Histologic evaluation using a standard hematoxylin and eosin stain demonstrated polymer remnants of cells embedded within collagen fibrils. The collagen bundle appeared to be organizing in a parallel fashion at the lateral aspects and appeared very similar to the collagen bundle seen in normal tendon. Centrally, the collagen fibrils appeared to be randomly oriented. Specimens that were created from implantation of parallel polymer fibers appeared to have a greater degree of parallel collagen fibril orientation at an earlier time period. The neo-tendon constructs demonstrated moderate tensile strength when stretched.

EXAMPLE 1

Construction of Neo-tendon

METHOD AND MATERIALS

Sheets approximately 100 microns thick composed of an embossed non-woven mesh of polyglycolic acid with interfiber interstitial spacing averaging 75 to 100 microns in diameter, arranged as either a random array of fibers, or as fibers in parallel (Dexon, Davis and Geck), were cut into pieces approximately 0.4 cm×4 cm and set aside. Tendon was obtained from the shoulder of newborn calves within six hours of sacrifice. The tendons were diced into pieces approximately 0.5 cm×0.5 cm and placed in a sterile 50 ml conical tube. The tendon pieces were washed twice with Dulbecco's phosphate buffered saline (PBS) (Gibco, Grand Island, N.Y.). A sterile 0.396 Collagenase solution was prepared by mixing 75 mg of type collagenase (Worthington, Freehold, N.J.) with 25 ml of Hamm's F-12 medium (Gibco, Grand Island, N.Y.). The tendon fragments were incubated in the collagenase solution for 12–16 hours at 37° C. on a shaker. After digestion, the solution was filtered through a sterile 150 micron nylon mesh (Tetko, Elmsford, N.Y.) to remove undigested fragments, and the tenocytes were washed twice in 25 ml of PBS. Cells were counted using a hemocytometer and concentrated in a cell suspension containing 150×10 tenocytes/ml. One hundred microliters of suspension (15 million cells) were then seeded onto each of 25 polymer constructs. Cell-polymer constructs were placed into 35 mm tissue dishes with 4 ml of Hamm's F-12 (Tissue Culture Media) with 1096 fetal calf serum (Gibco, Grand Island, N.Y.) with L-glutamine (292 $\mu$g/ml), penicillin (100 u/ml), streptomycin (100 $\mu$g/ml) and ascorbic acid (50 $\mu$g/ml) and kept in an incubator in vitro at 37° C. in the presence of 596 $CO_2$ for one week until the fibers were coated with multiple layers of tenocytes. Then, under general anesthesia, 25 cell-polymer constructs were surgically implanted subcutaneously into each of 25 nude mice (Athymic, NCr/nude/Sde, Dept. of Radiation Medicine at the Massachusetts General Hospital) four to five weeks of age (the experimental group). An additional 10 mice received implants of polymers containing no cells (the control group). Specimens were harvested after six to ten weeks of in vivo incubation and examined grossly and histologically for the evidence of tendon formation. The tensile mechanical property and handling characteristics of each specimen was assessed.

RESULTS

After six weeks, gross examination of all experimental specimens (n=25) closely resembled normal calf tendons from which the cells had been isolated. Histologic evaluation with hematoxylin and eosin and Masson's Trichrome staining demonstrates organized collagen fibrils with polymer remnants. The peripheral areas demonstrated a parallel linear organization of longitudinal collagen fibrils similar to the collagen bundles seen in normal calf tendon. Centrally, however, the collagen fibrils in this early specimens were randomly oriented and lacked the parallel linear organization. At 10 weeks, histological evaluation shows parallel linear organization of collagen bundles throughout the specimens, centrally and peripherally. Specimens created from implantation of tenocytes onto polymer fibers arranged in parallel fashion showed a greater degree of parallel collagen fibril organization at six weeks when compared to specimens created from randomly arranged polymer fibers, control specimens (n=10), without tenocyte implantation showed no evidence of tendon on gross or histological evaluation at ten weeks. Mechanical analysis of neo-tendon constructs have comparable tensile strength and similar mechanical characteristics to normal tendon. Tensile measurements showed that the tissue engineered tendons were very similar in mechanical behavior to that of normal tendons. The average tensile strength of the tissue engineered tendon after eight weeks in vivo was 10.75±2.29 MPa/normal tendon: 32.80±5.21 MPa standard deviation of that of the normal tendons. The mechanical loading was due solely to the new tendons formed, as the polymer scaffolds degrade and loss mechanical strength after four weeks.

The results demonstrate that tenocytes will adhere to synthetic biodegradable polymers survive and multiply in vitro, and that tenocyte-polymer construct implantation in vivo results in formation of tendon with characteristics similar to normal mature tendon. The collagen fibrils undergo organization over time. Histological evaluation of the neo-tendon construct at six weeks shows linear organization, like normal tendon, peripherally and random array of collagen fibrils centrally. With parallel arranged polymer fibers, linear orientation of collagen centrally was achieved at an earlier time. At ten weeks, the collagen fibers were arranged in parallel linear fashion throughout the showed proper anatomic cellular organization regardless of polymer fiber orientation. Thus, parallel structural fibers facilitates early organization of collagen, but the ultimate architectural organization is related to cellular communication and interaction and not of polymer orientation.

Variations and modifications of the present invention will be obvious from the foregoing detailed description of the invention. Such modifications and variations are intended to come within the scope of the following claims.

We claim:

1. A method to make new connective tissue construct, comprising:

seeding a matrix consisting of synthetic, biodegradable biocompatible polymer fibers of an appropriate length, thickness and strength with an interstitial spacing between approximately 50 and 300 microns which is suitable for implantation to form tendons or ligaments, wherein the polymer fibers degrade within less than one year after implantation, with dissociated connective tissue cells selected from the group consisting of cells obtained from tendons and cells obtained from ligaments, in an amount effective to form connective tissue following implantation into a patient in need thereof.

2. The method of claim 1 further comprising arranging the fibers in parallel prior to seeding, then implanting the construct into a patient in need thereof.

3. The method of claim 1 wherein the cells are selected from the group consisting of tenocytes and ligamentum cells.

4. The method of claim 1 wherein the polymer is selected from the group of polymers degrading over a period of less than twelve weeks consisting of poly(lactide), poly(glycolic acid), poly(lactide-co-glycolide), poly(caprolactone), polycarbonates, polyamides, polyanhydrides, polyamino acids, polyortho esters, polyacetals, degradable polycyanoacrylates, degradable polyurethanes, proteins, and polysaccharides.

5. The method of claim 1 wherein the construct is seeded with tenocytes and implanted to form new tendon.

6. The method of claim 1 wherein the construct is seeded with ligamentum cells and implanted to form new ligament.

* * * * *

UNITED STATES PATENT AND TRADEMARK OFFICE
CERTIFICATE OF CORRECTION

PATENT NO. : 6,123,727
DATED : September 26, 2000
INVENTOR(S) : Charles A. Vacanti et al.

It is certified that error appears in the above-identified patent and that said Letters Patent is hereby corrected as shown below:

<u>Title page,</u>
Item [56], under References Cited, please add the following three U.S. patent, and one reference:

|    |           |        |               |        |
|----|-----------|--------|---------------|--------|
| -- | 5,041,138 | 8/1991 | Vacanti et al. | 623/16 |
|    | 5,595,621 | 1/1997 | Light et al.   | 156/80 |
|    | 5,716,404 | 2/1998 | Vacanti et al. | 623/6  |

Cao et al., "Generation of Neo-Tendon Using Synthetic Polymers Seeded with Tenocytes," Transplantation Proceedings 6:3390-3391 (1994). --

Signed and Sealed this

Thirteenth Day of August, 2002

Attest:

Attesting Officer

JAMES E. ROGAN
Director of the United States Patent and Trademark Office